United States Patent [19]

Ikeda et al.

[11] Patent Number: 5,144,008
[45] Date of Patent: Sep. 1, 1992

[54] ARTIFICIAL CARRIER FOR IMMOBILIZATION OF BIOLOGICAL PROTEINS

[75] Inventors: Mikio Ikeda, Tachikawa; Shingo Morishita, Hachioji; Ichiro Matsuda, Hidaka, all of Japan

[73] Assignee: Fujirebio Inc., Tokyo, Japan

[21] Appl. No.: 603,022

[22] Filed: Oct. 26, 1990

[30] Foreign Application Priority Data

Oct. 27, 1989 [JP] Japan ................................. 1-278478

[51] Int. Cl.$^5$ ..................... A61K 37/12; A61K 39/00; G01N 33/544; C12N 11/08
[52] U.S. Cl. ..................................... 530/354; 436/528; 435/174; 435/177; 435/180; 424/85.8; 424/88; 525/54.1
[58] Field of Search ........................ 530/354; 514/21; 525/54.1; 435/174, 177, 180; 436/528; 424/85.8, 88

[56] References Cited

U.S. PATENT DOCUMENTS

| | | | |
|---|---|---|---|
| 4,013,468 | 3/1977 | Bergthaller et al. | 530/354 |
| 4,043,818 | 8/1977 | Himmelmann et al. | 530/354 |
| 4,066,636 | 1/1978 | Sera et al. | 530/354 |
| 4,067,741 | 1/1978 | Bergthaller et al. | 530/354 |
| 4,119,464 | 10/1978 | Sauerteig et al. | 530/354 |
| 4,134,770 | 1/1979 | Emoto et al. | 530/354 |
| 4,416,813 | 11/1983 | Ikeda et al. | 530/387 |

FOREIGN PATENT DOCUMENTS

| | | |
|---|---|---|
| 0054249 | 6/1982 | European Pat. Off. |
| 0106495 | 4/1984 | European Pat. Off. |
| 0158443 | 10/1985 | European Pat. Off. |
| 0275899 | 7/1988 | European Pat. Off. |
| 0363921 | 4/1990 | European Pat. Off. |

*Primary Examiner*—Robert A. Wax
*Assistant Examiner*—Richard C. Ekstrom
*Attorney, Agent, or Firm*—Wenderoth, Lind & Ponack

[57] ABSTRACT

An artificial carrier for immobilization of biological proteins, which are composed of particles comprising gelatin, an alkali metal metaphosphate and an anionic high-molecular electrolyte, said particles being water-insolubilized by a treatment with an aldehyde.

4 Claims, No Drawings

ARTIFICIAL CARRIER FOR IMMOBILIZATION OF BIOLOGICAL PROTEINS

This invention relates to a novel carrier for the immobilization of biological proteins such as antigens, antibodies, enzymes and the like, and to a process for production of the carrier.

In the field of serological tests, indirect passive hemagglutination using an antigen-antibody reaction is widely employed to diagnose various diseases. This reaction is based on the fact that the antigen or antibody, which is fixed on the surface of carrier particles, reacts with the corresponding antigen or antibody in a sample serum. As a result, agglutination of the particles takes place.

Non-biological particles, such as polystyrene latex, kaolin and carbon powders and biological particles, such as mammalian erythrocytes and microbial cells, may be used as carriers in the serological tests described above. Generally, non-biological particles are chemically stable, and are not antigenic. However, an antigen or an antibody cannot be tightly adsorbed onto a non-biological carrier. For example, when the carrier having an antigen or antibody adsorbed thereon (a sensitized carrier) is lyophilized for preservation purposes the antigen or antibody is released from the carrier particles. Consequently, the sensitized carrier must be preserved in the form of a suspension under low temperatures and in the absence of light, which inevitably leads to a short shelf life of the sensitized carrier.

Kaolin and carbon powders suffer from the disadvantage that it is difficult to obtain particles of uniform sizes. Polystyrene latex is deficient because it tends to aggregate spontaneously in a neutral pH range where indirect passive agglutination is usually carried out.

On the other hand, mammalian erythrocytes and microbial cells are biological particles which have substantially uniform sizes. However, their sizes depend on the species of animal or microorganism and accordingly, it is not always possible to obtain particles having a desired size. Among known biological carriers, mammalian erythrocytes are the most readily available and their sizes are uniform. However, their surfaces have specific antigenicity which can lead to nonspecific agglutination. Furthermore, it is difficult to obtain high quality erythrocytes due to variations of the biological, chemical and physical properties of the mammals from which the erythrocytes are obtained.

As a carrier in which such defects exhibited by those biological and non-biological carrier particles as above-described are improved, U.S. Pat. No. 4,416,813 (corresponding to European Patent 62,968) discloses artificial carrier particles comprising gelatin, a water-soluble polysaccharide and an alkali metal metaphosphate, which particles are insolubilized by treatment with an aldehyde. However, such water-soluble polysaccharides like arabic gum which are used in the preparation of above carrier particles are naturally occurring materials, and hence are subject to the defect that it is difficult to always secure constant quality. For example, carriers prepared with the use of water-soluble polysaccharides of different lots occasionally have a variance in particle diameters or electrophoresis characteristics. This invites the extra complication that qualitative analysis must be conducted for every lot of the water-soluble polysaccharide employed. Another problem is that yields also are low.

With a view towards developing an artificial carrier free of such defects, we have conducted extensive studies, and have discovered that when an anionic high-molecular electrolyte is used in the place of a water-soluble polysaccharide for preparing the artificial carrier, the above defects can be eliminated and an artificial carrier of a constant quality can be produced with good yields.

Thus, according to this invention, there is provided an artificial carrier for immobilization of biological proteins, which is in the form of particles comprising gelatin, an alkali metal metaphosphate and an anionic high-molecular electrolyte, which particles are water-insolubilized by treatment with an aldehyde.

The carrier of the present invention will be hereinafter explained in further detail.

The gelatin, any commercially available gelatin material may be used in the carrier of this invention, but from the standpoint of easily controlling the surface potential of the artificial carrier, acidic gelatins, inter alia, those having an isoelectric point at a pH between about 8 and 9, are preferred.

The alkali metal metaphosphate include the compounds expressed by the formula below, $$(MPO_3)_m$$

in which M stands for an alkali metal, preferably sodium or potassium, inter alia, sodium, and m is a number between 3 and 6. Specific examples of such compounds include sodium trimetaphosphate, sodium tetrametaphosphate, sodium hexametaphosphate, potassium trimetaphosphate, potassium tetrametaphosphate, potassium hexametaphosphate, and the like. Among those, the most preferred is sodium hexametaphosphate.

The anionic high-molecular electrolyte suitably used for preparing the artificial carrier of the present invention are the high molecular weight substances having anionic dissociative groups such as carboxylate, sulfate, sulfonate, phosphate, silicate and the like.

As specific examples of such anionic high-molecular electrolytes there may be named are high-molecular acid salts such as polyacrylates, polymethacrylates, polystyrenesulfonates, polyethylenesulfonates and polyvinylsulfates, polyacrylates being the most preferred. As those high molecular acid salts, alkali metal salts are preferred, those particularly preferred being sodium and potassium salts.

The molecular weight of the above anionic high-molecular electrolytes is not strictly critical but is variable over a wide range. Generally, however, those having number average molecular weights of 1,000–1,000,000, preferably 2,000–800,000, more preferably 200,000–800,000, can be advantageously used.

As the aldehyde to be used for water insolubilizing the particles composed of the aforesaid gelatin, an alkali metal metaphosphate and anionic high-molecular electrolyte, for example glutaraldehyde, formaldehyde, glyoxal, crotonaldehyde, acrolein, acetaldehyde, etc. may be named, glutaraldehyde being the most preferred.

The blend ratios of those components in the artificial carrier particles of the present invention are variable depending on such factors as the production conditions and physical properties required for the individual product, but generally the alkali metal metaphosphate can be present in the carrier in the range 0.1–100 parts, preferably 0.5–20 parts, inter alia, 1–10 parts, per 100 parts of the gelatin used; and the anionic high-molecular electrolyte can be present in the range 1-600 parts, preferably 5-300 parts, inter alia, 20-200 parts, per 100 parts of the gelatin, parts being by weight.

The carrier particles of the present invention may be colored, and hence can contain coloring agent. As the useful coloring agent for this purpose, for example, a red coloring agent like rhodamine, rose bengal, Ponceau 3R, Bordeaux S, fuchsine, eosine, neutral red, etc., and a blue coloring agent like crystal violet, toluidine blue, methylene blue, etc. may be named. Particularly reactive dyes like reactive red dye and reactive blue dye are preferred. Such coloring agent can normally be used in an amount ranging from 0.1-20 parts, particularly 0.5-5 parts, per 100 parts of gelatin, parts being by weight. While it is preferred that the coloring agent is dispersed in the carrier particles in advance, in certain cases it may be used for coloring already shaped particles.

The carrier of the present invention can be prepared, for example, by forming an aqueous solution containing gelatin, an alkali metal metaphosphate and an anionic high-molecular electrolyte at a temperature higher than the gelation temperature of said gelatin, adjusting the pH of said solution to a value of from pH4.5 to pH6, and then forming particles and treating said particles with an aldehyde to make them water-insoluble.

In preparing the carrier of the present invention, the first afore-described components are dissolved in an aqueous liquid medium such as water, to form an aqueous solution. The aqueous solution may also contain a water-miscible organic solvent. The water-miscible organic solvent may optionally be added to accelerate the precipitation of the gelatin particles. Such solvents include lower alcohols such as methanol, ethanol and isopropanol, and ketones such as acetone and methyl ethyl ketone, particularly methanol and ethanol being preferred.

Suitable concentrations of the components in the starting aqueous solution are as follows: the concentration of gelatin in the solution is preferably from 0.05 to 2% by weight, more preferably from 0.1 to 1.0% by weight; the concentration of the anionic high-molecular electrolyte is preferably from 0.01 to 0.5% by weight, more preferably from 0.05 to 0.25% by weight; and the concentration of the alkali metal metaphosphate is preferably from 0.5 to 20% by weight, particularly from 1 to 10% to dry weight of the gelatin. The preferred concentration of the water-miscible organic solvent is from 4 to 25 vol %. The concentration of the coloring agent may usually be about 0.0005 to 0.1% by weight.

The process for preparing the solution is subject to no critical limitations. For example, each component may be separately dissolved in warm water and then the resulting solutions are mixed. Alternatively, all components may be placed in a vessel and dissolved simultaneously. However, it is preferable that the water-miscible organic solvent, when used, is added later in order that good dispersion of the other components should be achieved.

Opacity may result when the pH of the solution is lower than the isoelectric point of gelatin, and therefore the pH of the solution should preferably be higher than the isoelectric point. It is normally preferred to adjust the pH of the solution to a range of pH8-10, preferably pH8.5-9.5, by adding an aqueous solution of, for example, sodium hydroxide, potassium hydroxide, etc. When any insoluble matter is present in the solution, it is normally desirable to remove the insoluble matter by such means as filtration, centrifuge, or the like.

The aqueous solution is usually kept at a temperature higher than the gelation temperature of gelatin. The gelation temperature depends on the concentration of the gelatin, etc. and it is usually about 0° to 60° C. Therefore, the temperature of the solution is preferably in the range of from 0° to 60° C., more preferably in the range of from 38° to 45° C.

Subsequently, the pH of the solution is adjusted to pH4 to 6, preferably pH4.5 to 5.5 by adding an acid, usually with stirring.

During the pH adjustment, particles are formed in the solution. In order to make the size of the particles uniform, an acid is added, preferably dropwise, to the solution, while the solution is preferably heated to 35° to 50° C. and stirred moderately. The optimal pH is selected from the range of pH2.5 to 6.0 depending on the desired size of particles and the composition of the solution on the individual occasion. For example, when the product particles are to be used as carriers for indirect passive hem agglutination, the preferred particle sizes are from 2 to 10 $\mu$m, in which case the optimal pH is in the range of from 4.0 to 5.5. The kind of acid to be used for the pH adjustment is not critical, which may be either inorganic or organic. However, a mild acid such as acetic acid is preferred to a strong or a weak acid.

No equilibrium relation exists between the particles formed by the pH adjustment and the mother liquor, and the particles do not disappear when the temperature of the solution is lowered below the gelation temperature of the gelatin. The particles are usually positively charged, although the charge which is carried depends on the ratio of gelatin to the anionic high-molecular electrolyte as well as on the surface condition of the particles. Metaphosphate ions are oriented and an electric double layer is constructed around the particles. This electric double layer makes the suspension of particles stable.

After the addition of the acid, the suspension of the particles may be immediately cooled to below 10° C., so that aggregation of the particles referred to in the earlier part may be prevented. Then, an aldehyde cross-linking agent is added to the suspension, and the particles are insolublized. This insolubilization may be achieved overnight, at a temperature below 10° C., preferably below 4° C., if desired. The amount of the cross-linking agent used may be from 0.1 to 200% upon the dry weight of the gelatin.

After the treatment with the cross-linking agent, the particles are recovered by, for example, centrifugation, etc., and may be washed twice or three times with water containing, if necessary, a surfactant.

The insolubilized particles thus produced may be used as a carrier for various purposes. However, the particles sometimes swell in a salt solution, and accordingly, it is preferred that the particles are further treated with the aldehyde cross-linking agent. For example, when the carrier is sensitized with antigen in a phosphate buffer solution, the carrier is preferably treated with formalin under the same conditions as those conventionally employed for treating erythrocytes. By such a treatment with formalin, the swelling tendency of the carrier is reduced, and the carrier also becomes preservable over a longer term because of the sterilizing effect of formalin.

The carrier of the invention can immobilize an antigen, antibody, enzyme and so on. As to the method of immobilization, for example, when antigen or antibody is sensitized on the carrier, the sensitization may be carried out in the manner similar to conventional sensitization procedures using mammalian erythrocytes as the carrier. [see, for example, Boyden, *J. Exp. Med.*, 93, 107-120 (1951)].

For example, the artificial carrier of the present invention can be converted to sensitized carrier by treating it with tannic acid and then causing it to adsorb sonicated *Treponema pallidum* (the causative agent of syphilis). Using this sensitized carrier, an agglutination image can be formed as the result of an immunoreaction thereof with the corresponding antibody possibly present in a sample serum, which allows a diagnosis of syphilis.

The capability of the invention is almost equal to that of mammalian erythrocytes which are considered the best carrier for indirect passive hem agglutination. Moreover, the present carriers are superior to mammalian erythrocytes because they are chemically and physically uniform and stable and have no antigenic activity. Furthermore, according to the process of the present invention, the carrier having a desired size is easily and inexpensively produced on a large scale.

The present invention is further illustrated by the following examples which are not intended to limit the scope of the invention.

EXAMPLE 1

Two grams of an acidic gelatin having an isoelectric point at pH 8.8 was dissolved in 48 g of water, heated to 40° C., and pH of the solution was adjusted to g using a 10 wt % sodium hydroxide solution. Separately, 1 g of sodium polyacrylate (degree of polymerization: 2,000-7,000, product of Wako Jun-yaku Co.) was dissolved in 49 g of warm water of 40° C. Thirty (30) g of the gelatin solution and 15 g of the sodium polyacrylate solution were poured into 154 ml of a 30 vol % aqueous ethanol solution which had been heated to 40° C. in advance, and the whole system was stirred thoroughly. A 10 wt % aqueous sodium hexametaphosphate solution 0.9 g was then added to the system, and into which 1 vol % aqueous acetic acid was added dropwise under stirring to reduce the pH to 5.2. The reaction liquid was cooled to a temperature no higher than 10° C. and to which 2.65 ml of 25 vol % aqueous gultaraldehyde was added, followed by 30 minutes' stirring and two nights standing to insolubilize the formed particles. The reaction liquid was centrifuged at 2,000 rpm for 15 minutes, whereby to recover the resultant particulate artificial carrier. The recovered artificial carrier particles had a diameter of about 3 $\mu$m.

Thus obtained artificial carrier was left in 4 vol % aqueous formalin for a week to reinforce its crosslinking.

EXAMPLE 2

The artificial carrier obtained in Example 1 was treated with tannic acid following Boyden method [*J. Exp. Med.* 93, 107-120 (1951)] and caused to adsorb thereonto sonicated Treponema pallidum, the causative agent of syphilis, to provide a sensitized artificial carrier.

EXAMPLE 3

The sensitized artificial carrier prepared in Example 2 was used in the indirect passive hem agglutination reaction by micro-titer method, in which serum samples of two syphilis-positive cases and one syphilis-negative case were used. The results were as shown in Table 1.

TABLE 1

| Serum Sample | Dilution ratio of Serum | | | | | | | |
|---|---|---|---|---|---|---|---|---|
| | 1:80 | 1:160 | 1:320 | 1:640 | 1:1280 | 1:2560 | 1:5120 | 1:10240 |
| Serum of positive case A | ++ | ++ | ++ | ++ | ++ | ++ | + | − |
| Serum of positive case B | ++ | ++ | ++ | + | − | − | − | − |
| Serum of negative case C | − | − | − | − | − | − | − | − |

++: judged positive
+: judged positive
−: judged negative

EXAMPLE 4

For comparing the performance of the sensitized artificial carrier prepared in Example 2, an animal erythrocyte carrier reagent (Serodia-TP, a commercial product of Fuji Rebio Co., Ltd.) and an artificial carrier prepared following Example 1 of U.S. Pat. No. 4,416,813 were sensitized with Treponema pallidum, the causative agent of syphilis, using serum of a positive case in the manner similar to above Example 3. Those sensitized carriers were used in the indirect passive hem agglutination reactions. The results were as shown in Table 2.

TABLE 2

| Reagent | Dilution ratio of Serum | | | | | | | |
|---|---|---|---|---|---|---|---|---|
| | 1:80 | 1:160 | 1:320 | 1:640 | 1:1280 | 1:2560 | 1:5120 | 1:10240 |
| Serodia-TP | ++ | ++ | ++ | ++ | ++ | ++ | + | − |
| Artificial carrier of U.S. Pat. No. 4,416,813 | ++ | ++ | ++ | ++ | ++ | ++ | + | − |
| Artificial carrier of the present invention | ++ | ++ | ++ | ++ | ++ | ++ | + | − |

++: judged positive
+: judged positive
−: judged negative

EXAMPLE 5

In order to demonstrate that according to the present invention artificial carrier of constant quality can be obtained irrelevantly to the lot number of the starting anionic high-molecular electrolyte employed, following experiment was conducted.

Using a sodium polyacrylate selected from five different lots (degree of polymerization: 2,000-7,000, product of Wako Jun-yaku Co.), artificial carriers of the present invention were prepared in the manner similar to Example 1.

For comparison, an arabic gum selected from five different lots (product of Wako Jun-yaku Co.) were used in place of above sodium polyacrlylate for preparing control artificial carriers in the manner similar to Example 1.

Average particle diameters and the results of electrophoretic mobility measurements of those carriers are shown in Table 3.

The electrophoretic mobility of the particles was measured using the Laser Zee syustem 3000 (manufactured by Pen Ken Inc., N.Y., U.S.A.). For this purpose about 1 ml of the suspension of the particles was placed in a cylindrical cell having a diameter of 1 mm and a length of 20 mm, and the mobility of the particles at 25° C. at a potential gradient of 1048 V/m was measured.

TABLE 3

| Characteristics | Carrier | | | | | | | |
|---|---|---|---|---|---|---|---|---|
| | Control artificial carrier | | | | Artificial carrier of the present invention | | | |
| | 1 | 2 | 3 | 4 | 5 | 6 | 7 | 8 |
| Particle diameter (μm) | 3.24 | 2.94 | 3.07 | 2.99 | 3.12 | 3.11 | 3.13 | 3.11 |
| Electrophoretic mobility (μm/sec/V/cm) | −0.754 | −0.802 | −0.747 | −0.771 | −0.826 | −0.824 | −0.821 | −0.828 |

What is claimed is:

1. An artificial carrier for immobilization of biological proteins, comprising a plurality of particles, said particles being comprised of an acid-treated gelatin, sodium hexametaphosphate and a high-molecular acid salt selected from the group consisting of polyacrylates, polymethacrylates, polystyrenesulfonates, polyethylenesulfonates and polyvinylsulfonates, and said particles being water-insolubilized by treatment with an aldehyde.

2. The carrier of claim 1 wherein the high-molecular acid salt is a sodium slat or potassium salt of polyacrylic acid.

3. The carrier of claim 1 wherein the aldehyde is glutaraldehyde.

4. A diagnostic reagent for use in serological testing, which comprises the artificial carrier of claim 1 which carries an antigen, an antibody or an enzyme.

* * * * *